(12) United States Patent
Gosselin et al.

(10) Patent No.: US 6,187,935 B1
(45) Date of Patent: Feb. 13, 2001

(54) METHOD FOR SEPARATING AN ORGANIC COMPOUND FROM AN AQUEOUS MEDIUM

(75) Inventors: Benoît Gosselin, Ophain; Michel Strebelle, Brussels, both of (BE)

(73) Assignee: Solvay SA (BE)

( * ) Notice: Under 35 U.S.C. 154(b), the term of this patent shall be extended for 0 days.

(21) Appl. No.: 09/530,915

(22) PCT Filed: Oct. 29, 1998

(86) PCT No.: PCT/EP98/07002

§ 371 Date: May 8, 2000

§ 102(e) Date: May 8, 2000

(87) PCT Pub. No.: WO99/24382

PCT Pub. Date: May 20, 1999

(30) Foreign Application Priority Data

Nov. 7, 1997 (BE) .................................................. 09700896

(51) Int. Cl.[7] .................................................. C07D 301/01
(52) U.S. Cl. ............................................................. 549/529
(58) Field of Search .............................................. 549/529

(56) References Cited

U.S. PATENT DOCUMENTS

| | | | |
|---|---|---|---|
| 4,562,264 | * 12/1985 | Gude et al. | 549/261 |
| 4,977,285 | * 12/1990 | Marquis et al. | 549/529 |
| 5,340,446 | * 8/1994 | Nelson et al. | 203/56 |

FOREIGN PATENT DOCUMENTS 0 100 119   2/1984   (EP) .

* cited by examiner

*Primary Examiner*—Amelia A. Owens
(74) *Attorney, Agent, or Firm*—Larson & Taylor, PLC

(57) ABSTRACT

Process for the manufacture of an organic compound in a water-containing liquid medium, according to which a mixture of reaction products comprising the organic compound, water and by-products is collected, at least a portion of the organic compound is separated from the mixture of reaction products, an effluent containing water and by-products is collected, an organic solvent is added to the effluent and the mixture containing the effluent and the solvent is subjected to a distillation treatment.

11 Claims, No Drawings

METHOD FOR SEPARATING AN ORGANIC COMPOUND FROM AN AQUEOUS MEDIUM

The present invention relates to a process for the manufacture of an organic compound, more particularly to a process for the treatment of effluents obtained after the separation of the organic compound from the reaction medium.

It is known, in particular from patent application EP-A-100119, to convert an olefin compound (that is to say an organic compound containing at least one carbon-carbon double bond) to the corresponding oxirane by reaction with hydrogen peroxide in a liquid medium containing water. This process makes it possible, for example, to synthesize 1,2-epoxypropane (propylene oxide) or 1,2-epoxy-3-chloropropane (epichlorohydrin) starting with propylene or allyl chloride respectively.

In this known process, the mixture of reaction products obtained on leaving the epoxidation reactor contains oxirane, water, various reaction by-products and possibly unconverted reagents as well as, most often, a diluent (for example methanol or acetone). Among the by-products are products which are formed by the reaction between oxirane and water or, where appropriate, the diluent. For example, when this process is applied to the synthesis of epichlorohydrin by the reaction between allyl chloride and hydrogen peroxide in methanol and water, the epichlorohydrin and the water (or the methanol) can form, under the usual epoxidation conditions, notable quantities of 1-chloro-3-methoxy-2-propanol, 1-chloro-2-methoxy-3-propanol, 1,3- dichloro-2-propanol, 2,3-dichloropropanol and 1-chloro-2,3-dihydroxypropane. Starting with propylene, the formation of propylene glycol as well as 1-methoxy-2- propanol and 2-methoxy-1-propanol is observed. These by-products are soluble in water and are hence found in the aqueous effluent which is collected after the separation of the oxirane from the reaction medium. Some of the water-soluble by products (in particular the 1-chloro-3-methoxy-2-propanol and 1,3-dichloro-2- propanol) form azeotropes with water. They cannot therefore be easily separated by distillation or by stripping. In addition, these by-products pose problems of discharge because they contribute to the chemical oxygen demand and, where appropriate, to the presence of undesirable halogenated compounds.

The subject of the invention is a simple process for the manufacture of an organic compound in a water-containing liquid medium, which makes it possible to eliminate the water-soluble by-products easily and with a high efficiency and to thereby reduce the problems of discharge.

The invention therefore relates to a process for the manufacture of an organic compound in a water-containing liquid medium, according to which a mixture of reaction products comprising the organic compound, water and by-products is collected, at least a portion of the organic compound is separated from the mixture of reaction products, an effluent containing water and by-products is collected, an organic solvent is added to the effluent and the mixture containing the effluent and the solvent is subjected to a distillation treatment. The organic solvent used in the process according to the invention allows the extraction of the by-products from the water and their elimination by azeotropic distillation.

The process according to the invention is quite suitable when the by-products contain one or more hydrophilic groups. It is particularly suitable when the by-products contain one or more hydroxyl groups. These by-products mostly are hydroxylated compounds formed by opening of the epoxide cycle. The best results are obtained when the by-products contain, in addition, one or more halogenated groups. The process according to the invention is particularly applicable to the elimination of by-products such as diols and/or their monoalkyl ether derivates.

The process according to the invention is particularly applicable to the manufacture of an oxirane. In this case, an olefin compound is reacted with a peroxide compound in a water-containing liquid medium, a mixture of reaction products comprising the oxirane, water and by-products is collected, at least a portion of the oxirane produced is separated from the mixture of reaction products, an effluent containing water and by-products is collected, an organic solvent is added to the effluent and the mixture containing the effluent and the solvent is subjected to a distillation treatment.

In the process according to the invention, there may be collected after distillation of the effluent, on the one hand, at the distillation front, a first liquid phase containing the solvent and a second liquid phase containing water purified with respect to the by-products and possible traces of solvent, and on the other hand, at the distillation base, a mixture of solvent and by-products. The two distinct liquid phases collected at the distillation front can be separated according to conventional separation methods such as decantation. Thus, the first liquid phase containing the solvent which can be recycled into the distillation, as it is or after it has been subjected to a purification treatment, is recovered on the one hand. On the other hand, the second liquid phase, containing the water purified with respect to the by-products and possible traces of solvent, which may be optionally subjected to stripping in order to recover the possible traces of solvent which can be recycled into the distillation, is recovered. Next, the distillation base, which contains a mixture of solvent and by products, may also be subjected to evaporation, optionally under vacuum, in order to recover the solvent in the purified state and to recycle it into the distillation.

The solvent may contain one or more compounds. Generally, a solvent is used which has a very low miscibility with water. A solvent which is substantially stable and chemically inert towards the constituents of the aqueous effluent under the distillation conditions, as well as, where appropriate, in the subsequent steps is particularly suitable.

Solvents which give good results are those whose specific gravity differs from that of the liquid phase containing the purified water collected at the distillation front by at least 0.02 g/cm$^3$, in particular by at least 0.04 g/cm$^3$. The best results are obtained when these specific gravity values differ by at least 0.05 g/cm$^3$.

It may prove advantageous to use a solvent whose boiling point is low compared with the above-mentioned by-products. This indeed makes it possible to subject the distillation base to a separation of the solvent from the by-products by evaporation, optionally under vacuum, to thereby purify the solvent and to recycle it into the distillation. Solvents are normally used whose boiling point differs from that of the water-soluble by-products by at least 5°C., in particular by at least 10°C. The best results are obtained when these boiling points differ by at least 15° C.

Compounds which may be used as solvent in the process according to the invention are the aliphatic or aromatic organic derivatives which may include atoms such as oxygen and/or a halogen, as well as mixtures thereof. There may be mentioned by way of examples alkylated aromatic hydrocarbons carrying one or more alkyl groups containing from 1 to 4 carbon atoms such as toluene, xylene, mesitylene, ethylbenzene and butylbenzene. Xylene is particularly preferred. Xylene is understood to mean either each of the isomers (ortho, meta or para) or mixtures thereof. There may also be mentioned the saturated aliphatic hydrocarbons containing from 5 to 12 carbon atoms such as pentane, hexane, octane and decane, as well as cyclic aliphatic hydrocarbons such as decalin.

The distillation process according to the invention is carried out according to conventional azeotropic distillation methods. Advantageously, an azeotropic distillation column is used as distillation apparatus.

The pressure at which the distillation is carried out is not critical. The distillation is generally carried out at a pressure which may vary from a subatmospheric pressure to 7600 mm Hg. The pressure is advantageously at least equal to 0.5 mm Hg. It is advantageously at most equal to 3800 mm Hg.

The temperatures at the distillation front and base depend on the solvent used and the pressure applied. In practice, at atmospheric pressure, the temperature at the distillation front is at least 30° C. and less than 100° C.

The weight ratio between the solvent and the effluent depends on the solvent used and the distillation apparatus used. In practice, the weight ratio between the solvent and the effluent is generally at least 0.01. Preferably, it is at least 0.1. This ratio usually does not exceed 5. Most often, it does not exceed 1. Good results were obtained with a ratio of 0.1 to 1.

The effluent generally contains at least 1% by weight of by-product, in particular at least 5% by weight. Most often, the effluent contains at least 10% by weight of by-product. The by-product concentration generally does not exceed 50% by weight of the effluent, in particular does not exceed 30% by weight. The effluent most often contains less than 20% by weight of by-product.

Oxirane, which may be prepared by the process according to the invention, is an organic compound corresponding to the general formula:

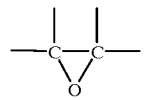

Oxirane generally contains from 2 to 20 carbon atoms, preferably from 3 to 10 carbon atoms. It may contain halogen atoms, in particular chlorine. An olefin compound which is quite suitable in the process according to the invention is allyl chloride. The olefin compounds may also be chosen from the α-olefins. There may be mentioned, byway of examples, propylene, 1-octene and 1-decene. Propylene is quite suitable. An oxirane which may be advantageously prepared by the process according to the invention is epichlorohydrin. It is also possible to manufacture propylene oxide.

The peroxide compound which may be used in the process according to the invention may be chosen from hydrogen peroxide and any peroxide compound containing active oxygen and capable of bringing about an epoxidation but preferably except hydroperoxide. There may be mentioned, by way of examples, the peroxide compounds obtained by oxidation of organic compounds such as ethylbenzene, isobutane and isopropanol. Hydrogen peroxide is preferred.

In the process according to the invention, the step for separating at least a portion of the organic compound from the mixture of reaction products may be carried out by bringing this mixture into contact with an extracting organic liquid so as to obtain two distinct liquid phases, namely, on the one hand, an organic extract containing most of the quantity of oxirane produced, and, on the other hand, an aqueous raffinate containing water and the water-soluble by-products.

The process according to the invention has proved to be very advantageous for preparing 1,2-epoxy-3-chloropropane by the reaction between allyl chloride and hydrogen peroxide. It is also suitable for the preparation of 1,2-epoxypropane by the reaction between propylene and hydrogen peroxide.

The examples which follow are intended to illustrate the present invention without, however, limiting its scope.

EXAMPLE 1 (in accordance with the invention)

An aqueous effluent coming from the synthesis of epichlorohydrin starting with allyl chloride and hydrogen peroxide which contains 59.5 g/kg of 1-chloro-3- methoxy-2-propanol and 2.8 g/kg of 1,3-dichloro-2-propanol was brought into contact with 135 g of xylene/kg of effluent to be treated. This mixture was subjected to distillation in a Vigreux column 1 m in height. The temperature measured at the front of the distillation column was 45–49° C. and the absolute pressure in the column was 100 mm Hg. After separation of the phases at the distillation front, a purified aqueous phase was recovered which represents 84.5% of the aqueous effluent used and which was analysed. Table I gives the recovery ratio for each ofthe two by-products. products. The recovery ratio is the ratio (expressed in %) between the weight of the in question present in the purified aqueous phase and the weight of this by-product present in the aqueous effluent before distillation.

TABLE I

| | |
|---|---|
| 1-chloro-3-methoxy-2-propanol | 1.8 |
| 1,3-dichloro-2-propanol | 0.3 |

EXAMPLE 2 (not in accordance with the invention)

The same aqueous effluent as in Example 1, except that it contains 96.1 g/kg of 1-chloro-3-methoxy-2-propanol and 4.2 g/kg of 1,3-dichloro-2-propanol, was subjected to distillation in the same apparatus as in Example 1 but without addition of xylene. The temperature measured at the front of the distillation column was 20–30° C. and the absolute pressure in the column was initially 30 mm Hg and then decreased to 1 mm Hg. After distillation, an aqueous phase was recovered which represents 70.7% of the aqueous effluent used and which was analysed. Table II gives the recovery ratio for each of the two by-products.

TABLE II

| | |
|---|---|
| 1-chloro-3-methoxy-2-propanol | 52.4 |
| 1,3-dichloro-2-propanol | 65.1 |

What is claimed is:
1. A process for the manufacture of an oxirane by reaction between an olefin compound and hydrogen peroxide in a water-containing liquid medium, according to which a mixture of reaction products comprising the oxirane, water and hydroxylated by-products formed by the opening of the oxirane ring is collected, at least a portion of the oxirane is separated from the mixture of reaction products, an effluent containing water and by-products is collected, an organic solvent, which presents a very low miscibility with water and which is capable of extracting the by-products from the aqueous effluent, is added to the effluent and the mixture containing the effluent and the solvent is subjected to a distillation treatment.

2. The process according to claim 1, in which the solvent is not miscible with water.

3. The process according to claim 2, in which the by-products contain, in addition, one or more halogenated groups.

4. The process according to claim 1, in which there are collected after distillation, on the one hand, at the distillation front, a first liquid phase containing the solvent and a second liquid phase containing water purified with respect to the by-products and possible traces of solvent, and on the other hand, at the distillation base, a mixture of solvent and by-products, the two liquid phases collected at the distillation front are separated, and the first liquid phase containing the solvent is recycled into the distillation.

5. The process according to claim 4, in which the specific gravity of the solvent differs from that of the liquid phase containing the purified water collected at the distillation front by at least 0.04 g/cm$^3$.

6. The process according to claim 1, in which the boiling point of the solvent differs from that of the by-products by at least 5° C.

7. The process according to claim 1, in which the solvent is chosen from the aliphatic or aromatic organic derivatives which may include atoms oxygen and/or a halogen, as well as mixtures thereof.

8. The process according to claim 7, in which the solvent is chosen from alkylated aromatic hydrocarbons carrying one or more alkyl groups containing from 1 to 4 carbon atoms, aliphatic saturated hydrocarbons containing from 5 to 12 carbon atoms, and aliphatic cyclic hydrocarbons.

9. The process according to claim 8, in which the solvent is chosen from toluene, xylene, mesitylene, ethylbenzene and butylbenzene.

10. The process according to claim 1, in which the distillation base, which contains a mixture of solvent and by-products, is subjected to evaporation, optionally under vacuum, in order to recover the solvent in the purified state, and to recycle it into the distillation.

11. The process according to claim 1 in which the oxirane is 1,2-epoxy-3-choropropane or 1,2-epoxypropane, and the olefin compound is allyl chloride or propylene.

* * * * *